(12) United States Patent
Marsala et al.

(10) Patent No.: US 6,430,994 B1
(45) Date of Patent: Aug. 13, 2002

(54) PROCESS FOR THE CONTINUOUS DETERMINATION OF THE INTERACTION BETWEEN DRILLING FLUIDS AND SHALE FORMATIONS

(75) Inventors: Alberto Marsala, Bergamo; Stefano Carminati, Monza, both of (IT)

(73) Assignees: ENI S.p.A., Rome; Enitecnologie S.p.A., San Donato Milanese, both of (IT)

( * ) Notice: Subject to any disclaimer, the term of this patent is extended or adjusted under 35 U.S.C. 154(b) by 0 days.

(21) Appl. No.: 09/721,649

(22) Filed: Nov. 27, 2000

(30) Foreign Application Priority Data

Nov. 26, 1999 (IT) .......................................... MI99A2476

(51) Int. Cl.7 .......................... E21B 49/00; E21B 43/17
(52) U.S. Cl. ...................... 73/152.23; 166/308; 166/597
(58) Field of Search ........................ 73/152.16, 152.06, 73/152.23, 152.52, 152.53; 166/308, 597, 598, 627

(56) References Cited

U.S. PATENT DOCUMENTS

| | | | | | |
|---|---|---|---|---|---|
| 5,345,819 A | * | 9/1994 | Dearing | .................... | 73/152.23 |
| 5,511,615 A | * | 4/1996 | Rhett | ....................... | 166/250.1 |
| 5,679,885 A | * | 10/1997 | Lenormand et al. | ........... | 73/38 |
| 5,741,971 A | * | 4/1998 | Lacy | ........................... | 73/597 |

* cited by examiner

Primary Examiner—Hezron Williams
Assistant Examiner—Jay Politzer
(74) Attorney, Agent, or Firm—Oblon, Spivak, McClelland, Maier & Neustadt, P.C.

(57) ABSTRACT

Process for the continuous determination of the interaction between drilling fluids and shale formations, which comprises:

(a) preparation of a water- or oil-based drilling fluid;
(b) preparation of a shale sample having at least two flat, parallel opposite surfaces;
(c) preparation of the mixture of (b) and (a);
(d) continuous measurement of the ultrasonic wave transmission velocity through the sample (c), and variations in thickness (swelling and shrinking) of the shale sample, due to interaction with the drilling fluid (a).

6 Claims, 3 Drawing Sheets

Schematic diagram of the apparatus
A : Cutting
B : Pulse generator
C : Emitter & Receiver
D : Emitter
E : Oscilloscope

*FIG. 1* Schematic diagram of the apparatus

A : Cutting
B : Pulse generator
C : Emitter & Receiver
D : Emitter
E : Oscilloscope

PROCESS FOR THE CONTINUOUS DETERMINATION OF THE INTERACTION BETWEEN DRILLING FLUIDS AND SHALE FORMATIONS

BACKGROUND OF THE INVENTION

Field of the Invention

The present invention relates to a process for the continuous determination of the interaction between drilling fluids and shale formations.

More specifically, the present invention relates to a process for continuously verifying the effect of drilling fluids on the stability of shale formations in oil well drilling, by measuring the ultrasonic wave transmission velocity on clay cuttings subjected to aging in drilling fluids.

DISCUSSION OF THE BACKGROUND

During the drilling of an oil well, there is often the problem of instability of the well in shale formations. To prevent this instability, drilling fluids are prepared with additives suitable for maintaining (or if possible improving) the mechanical properties of the shales and inhibiting swelling. The effectiveness of these additives is evaluated by tests which are specified in API procedures, for example, dispersion tests of clay cuttings in mud (hot-rolling test) or laboratory procedures (for example measuring the swelling of clay samples). On the other hand, techniques for evaluating the mechanical characteristics (for example uniaxial or triaxial creep tests) have the great disadvantage of being destructive, costly and time-consuming.

None of these techniques considers the possibility of analyzing the mechanical behavior of shale interacting with a drilling fluid in relation to time, a fundamental factor in evaluating the arising of instability in shale formations during the drilling of oil wells.

It is also known that the relative mechanical properties can be determined from the velocity of sound waves through rock samples. Although these acoustic techniques are not destructive, they have the drawback of being used at present only for the acoustic characterization of formations and although they detect the mechanical properties of the rock, they neglect, on the other hand, the effect due to rock-drilling fluid interaction.

SUMMARY OF THE INVENTION

A process has now been found which overcomes the above disadvantages, as it allows the mechanical properties of shales to be evaluated in the presence of drilling fluids in relation to the interaction time. The process of the present invention also has the advantage of not being destructive.

In accordance with this, the present invention relates to a process for the continuous determination of the inter-action between drilling fluids and shale formations, which comprises:

(a) preparation of a water- or oil-based drilling fluid;
(b) preparation of a shale sample having at least two flat, parallel opposite surfaces;
(c) preparation of the mixture of (b) and (a);
(d) continuous measurement of the ultrasonic wave transmission velocity through the sample (c), and variations in thickness (swelling and shrinking) of the shale sample, due to interaction with the drilling fluid (a).

The process of the present invention can be applied to cuttings produced during drilling, or to shale samples prepared by suitably cutting well or outcrop cores. Alternatively, it is possible to operate on reconstituted shale samples.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENT

The water- or oil-based drilling fluids and relative preparation (step a) are well-known to experts in the field (see for example Gray G. R. and Darley H. C. H.: "Composition and properties of oil well drilling fluids"; Gulf Publishing Company, fourth edition, Houston Tex. U.S.A., 1980).

Step (b) of the process of the present invention consists of the preparation of the shale sample. This is carried out by cutting suitably-sized (at least 2 mm thick) test-samples. When cuttings are used, these can either be derived from wells or be prepared from cores (well or out-crop). Cuttings are normally prepared with an automatic slitter in demineralized water or oil to obtain the desired test-samples, which must have at least two flat, parallel surfaces. Those which have cracks are discharged. It is essential for them not to be exposed to the air as the response of the sample greatly depends on the degree of saturation. When well cuttings are used, owing to their irregular geometry, they must be subjected to smoothing or cutting until two flat, parallel surfaces are obtained. This can be achieved by smoothing each cutting by means of a diamond sandpaper disk lubricated with oil or demineralized water, until two flat, parallel surfaces are obtained.

Step (c) consists in preparing the mixture of (a)+(b), preferably prepared by pouring (b) into (a), under the desired temperature conditions, indicatively from 5° C. to 90° C., preferably from 20° C. to 60° C.

Figure 1:
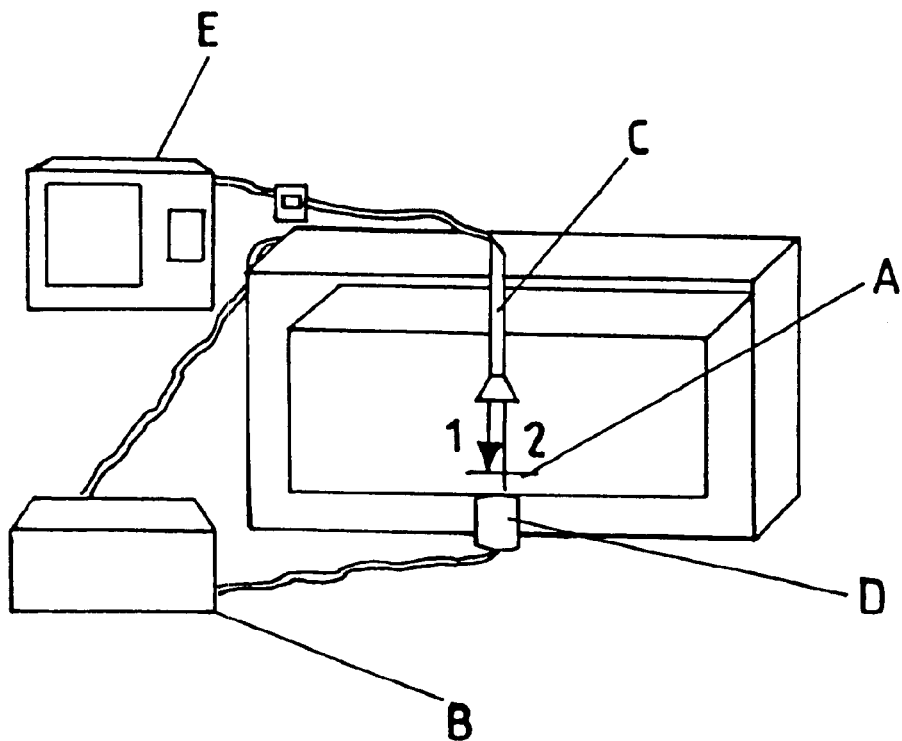
FIG. 1 is a schematic diagram of the apparatus of the present invention.

In step (d) the continuous measurement of the compressional wave transmission velocity is carried out on clay cuttings immersed in a fluid (drilling mud or other). The equipment used is indicated, for illustrative purposes, but without limiting the scope of the invention, FIG.1.

The clay cutting is placed inside the container filled with the fluid with which it interacts, and set on the signal emitter transducer. The other transducer (which acts as emitter and receiver) is placed near the other side of the cutting. With this configuration, it is possible to run two simultaneous measurements whose combined results enable two values to be determined:

a) the transit time of the ultrasounds reflected by the surface of the cutting (in FIG. 1 indicated by 1) from which the variations in the thickness of the cutting are continuously determined during the interaction test (possible swelling or shrinking measurement of the clay);

b) the transit time through the clay cutting (in FIG. 1 indicated by 2) from which the compressional wave transmission velocity measurement is continuously obtained.

Variations in these measurements indicate complete interaction between fluid and shale. The variation in the velocity in the clay cutting indicates a variation in its mechanical properties. This is confirmed by comparison with the mechanical indentation index values measured on the same shale cuttings subjected to interaction. A comparative example is provide to sustain this confirmation.

The following examples are provided for a better understanding of the present invention.

EXAMPLE 1

Figure 2:
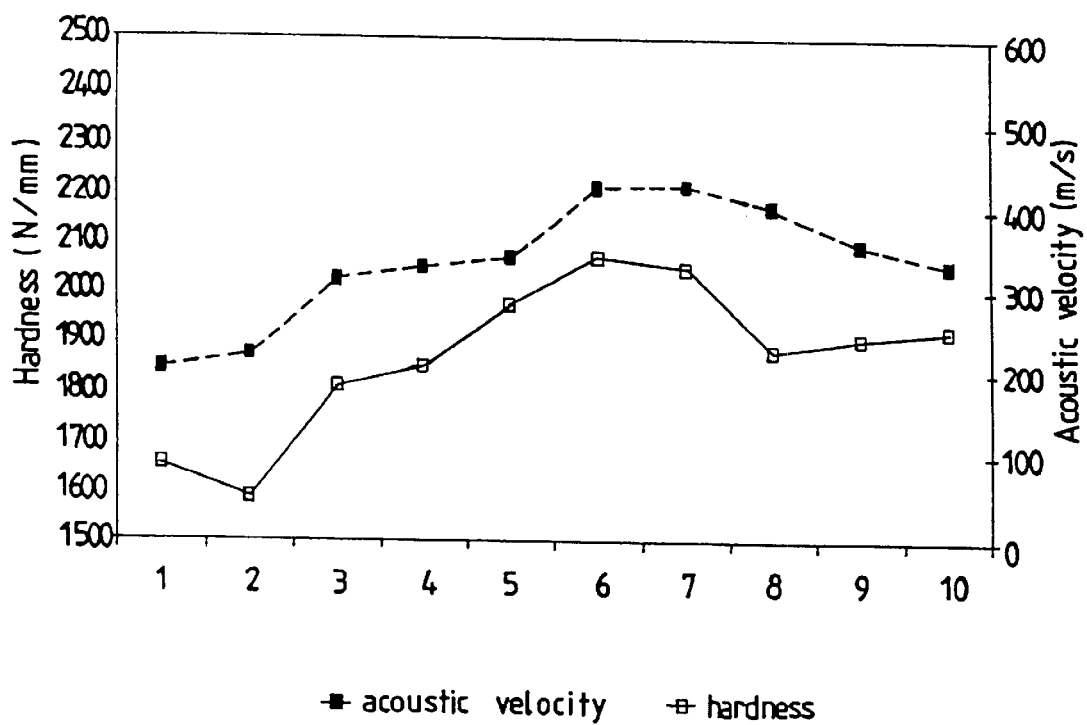
FIG. 2 shows an example of the acoustic velocity values obtained using the process of the present invention.

FIG. 2 indicates the acoustic velocity values obtained according to the process of the present invention, of samples of Pierre Shale 2 aged in the solutions specified in the table. The same figure indicates, for comparative purposes, the hardness values obtained with a destructive test, i.e., with the indentation test, on the same samples of Pierre Shale 2 on which acoustic measurements had been previously run (the indentation test is carried out by measuring the force applied to a point with a diameter of 1 mm to penetrate the shale by 0.3 mm at a rate of 0.01 mm/s and gives a direct indication of the hardness of the rock, and consequently of the mechanical stability of the shale formation).

A good correspondence is observed between acoustic velocity and hardness of the cutting for the various samples aged in the solutions specified in the table. This indicates that the acoustic velocity measurements can be used to evaluate the mechanical characteristics of shale and consequently evaluate the impact of the drilling fluid on the stability of the drilling well walls.

| Sample # | Composition (concentration additives in wt %) | | | | | |
|---|---|---|---|---|---|---|
| | silicate-Na | soltex-Na | ZRC | pac-lv | ester | KCl |
| 1 | 0 | 0 | 0.6 | 1 | 0.4 | 0 |
| 2 | 0 | 6 | 0 | 0 | 0 | 0 |
| 3 | 0 | 6 | 0 | 1 | 0 | 10 |
| 4 | 0 | 6 | 0.6 | 0 | 0.4 | 10 |
| 5 | 10 | 0 | 0 | 0 | 0 | 0 |
| 6 | 10 | 0 | 0 | 1 | 0.4 | 10 |
| 7 | 10 | 0 | 0.6 | 0 | 0 | 10 |
| 8 | 10 | 6 | 0 | 0 | 0.4 | 10 |
| 9 | 10 | 6 | 0 | 1 | 0.4 | 0 |
| 10 | 10 | 6 | 0.6 | 0 | 0 | 0 |

The additives used in the formulation of the drilling fluid, indicated below, were subdivided into use classification.

CLAY INHIBITORS
 ** Avasilix® 22, AVA: sodium silicate (Silicate-Na);
 ** Soltex®, AVA: modified asphaltene (Soltex-Na);
 ** KCl DISPERSING AGENT
 ** Rheomate®, Lamberti: Zirconium citrate (ZRC)

FILTRATE REDUCER
 ** PAC-LV, Baroid: polyanionic cellulose

LUBRICANT
 ** Avagreen Biolube, AVA: ester.

EXAMPLE 2

Figure 3:
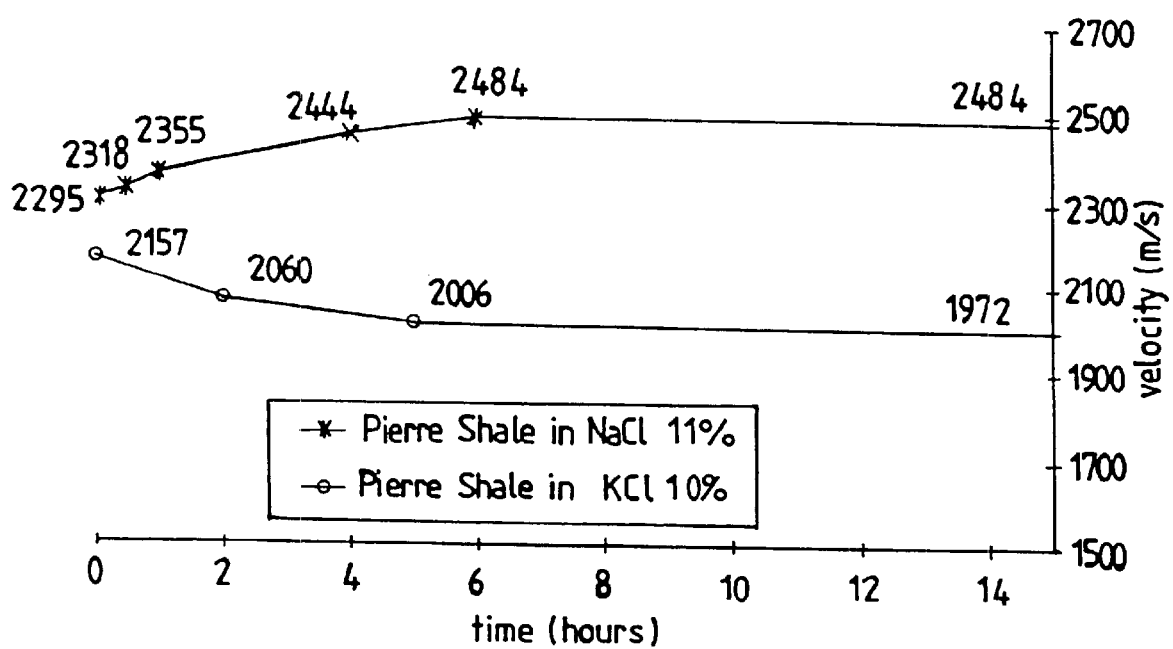
FIG. 3 shows an example of the change in the compression wave transmission velocities over time using the process of the present invention.

FIG. 3 indicates the trend of the compressional wave transmission velocities through two cuttings of Pierre Shale 2 immersed in two different aqueous solutions, specifically 11% of Sodium Chloride solution (NaCl) and 10% of Potassium Chloride (KCl). The trend shows how the interaction takes place during the first 5–6 hours, and is then stabilized. This result agrees with what is calculated by means of the diffusion coefficient of a fluid inside the Pierre Shale 2 clay (the size of the samples is a 5 mm-side cube). The trend of the velocity variation through samples of Pierre Shale 2 in contact with the two different fluids also indicates different effects (increase in the one case and decrease in the other) on the mechanical properties following said physicochemical interactions.

What is claimed is:

1. A process for the continuous determination of the interaction between drilling fluids and shale formations, the process comprising:

(a) preparing a water- or -oil-based drilling fluid;
   (b) preparing a shale sample having at least two flat, parallel opposite surfaces;
   (c) combining the prepared shale sample of (b) with the prepared drilling fluid of (a) into a combined sample;
   (d) predicting a hardness of the shale formations without applying a stress to the combined sample by (1) ultrasonically measuring variations in thickness of the shale sample in the combined sample, and (2) measuring ultrasonic wave transmission velocity through the combined sample.

2. The process according to claim 1, wherein the shale is selected from cuttings produced during drilling.

3. The process according to claim 1, wherein the drilling fluids are water-based.

4. The process according to claim 1, wherein the process is carried out at a temperature ranging from 5° C. to 90° C.

5. The process according to claim 4, wherein the temperature ranges from 20° C. to 60° C.

6. The process according to claim 1, wherein the measurement (d) is effected using a container inside which the combined sample of (a) and (b), an ultrasonic wave emitter and receiver, and an ultrasonic wave emitter are placed, and wherein outside the above container, there being a signal generator and a wave analyzer.

* * * * *